US006071257A

United States Patent [19]

Stojanovic

[11] Patent Number: 6,071,257

[45] Date of Patent: Jun. 6, 2000

[54] LINKABLY SEGMENTED DEVICE HAVING PROTRUDING CONTACT ELEMENTS

[76] Inventor: Branislov Stojanovic, Dragoslava Stojanovica 6, 2100 Novi Sad, Yugoslavia

[21] Appl. No.: 08/886,845

[22] Filed: Jul. 1, 1997

Related U.S. Application Data

[63] Continuation of application No. 08/404,347, Mar. 15, 1995, abandoned, which is a continuation-in-part of application No. 08/322,060, Oct. 12, 1994, Pat. No. 5,498,233, which is a continuation of application No. 07/855,772, Mar. 23, 1992, abandoned.

[30] Foreign Application Priority Data

Mar. 22, 1991 [YU] Yugoslavia ................................ 505/91

[51] Int. Cl.$^{7}$ ........................................................ A61F 5/02

[52] U.S. Cl. ................................ 602/19; 602/18; 128/845

[58] Field of Search .............................. 601/23; 606/201, 606/204, 240; 602/13, 18, 19; 600/9, 12–15; 402/105; 2/92; 128/845, 781, 907

[56] References Cited

U.S. PATENT DOCUMENTS

| | | | |
|---|---|---|---|
| 2,447,698 | 10/1948 | Haberer . | |
| 4,230,099 | 10/1980 | Richardson . | |
| 4,411,258 | 10/1983 | Pujals, Jr. | 606/204 |
| 4,716,898 | 1/1988 | Chauve et al. . | |
| 4,760,842 | 8/1988 | Holmes . | |
| 5,007,633 | 4/1991 | Lemire . | |
| 5,035,017 | 7/1991 | Komuro . | |
| 5,048,509 | 9/1991 | Grundei et al. . | |
| 5,120,288 | 6/1992 | Sinaki . | |
| 5,140,995 | 8/1992 | Uhl . | |
| 5,158,073 | 10/1992 | Bukowski | 606/204 |
| 5,267,497 | 12/1993 | James et al. . | |
| 5,290,307 | 3/1994 | Choy . | |
| 5,312,350 | 5/1994 | Jacobs | 606/201 |
| 5,328,447 | 7/1994 | Kapounek et al. | 602/19 |
| 5,437,614 | 8/1995 | Grim | 602/19 |

FOREIGN PATENT DOCUMENTS

| | | |
|---|---|---|
| 120697 | 5/1901 | Germany . |
| 2128410 | 12/1972 | Germany . |
| 2334500 | 1/1975 | Germany . |
| 2506647 | 10/1976 | Germany . |
| 3525521 A1 | 1/1987 | Germany . |
| 1120-997-A | 10/1984 | U.S.S.R. . |
| 2193429 | 2/1988 | United Kingdom . |

*Primary Examiner*—Jeanne M. Clark
*Attorney, Agent, or Firm*—Baker & McKenzie

[57] ABSTRACT

A device for being externally positioned on a body of a person having linkable segments with protruding contact elements. The device preferably is flexible and may have flexible linkages such that the segments may be linked side-by-side, or end-to-end. Alternatively, the device may have a single segment, having a plurality of contact elements and an apparatus for positioning the device on the wearer.

35 Claims, 7 Drawing Sheets

LINKABLY SEGMENTED DEVICE HAVING PROTRUDING CONTACT ELEMENTS

This is a continuation of application Ser. No. 08/404,347 filed on Mar. 15, 1995, now abandoned, which was a continuation-in-part of U.S. patent application Ser. No. 08/322,060, filed on Oct. 12, 1994 and issued as U.S. Pat. No. 5,498,233, from which priority is also claimed and which was a continuation of U.S. patent application Ser. No. 07/855,772, filed Mar. 23, 1992, now abandoned, and from which priority also is claimed.

BACKGROUND OF THE INVENTION

The present invention relates to a device to be applied externally to the body of a person, typically to the back or adjacent to the spinal column, but which also may be applied to other parts of the body, such as joints.

Various types of devices for physiological or psychological treatment of a person's musculature, joints or spinal system are known. Some of those devices take the form of back braces for straightening the spinal column. Others are for applying pressure in order to create a heating or massaging type of effect. Some such devices are mechanized so as to apply a vibratory pressure or active heating. Others apply pressure passively.

It is known that massaging or using devices applied externally to the body can impart pressure and otherwise have a soothing and/or pain relief effect. One typical pressure application device is illustrated in German Disclosure No. 2,128,410. Such a device provides a backbone to which discreet brackets are mounted. Each of the brackets has two support surfaces for applying pressure or support to the back of the person wearing the device. Such devices suffer disadvantages of being rigid and thereby failing to contour to the shape of the body of the wearer. Furthermore, they typically lack flexibility for easily increasing or decreasing the size of the area for application of pressure or other treatment.

Another type of pressure application device is illustrated in U.S. Pat. No. 4,716,898. In that device, a "stimulating member" for applying pressure to acupuncture points is rigidly connected to a belt device for keeping the member pressed onto a desired portion of a body.

SUMMARY OF THE INVENTION

The present invention alleviates to a great extent the disadvantages of the known devices by providing linkable segments having protruding contact elements, for being applied externally to the body of a person. Each of the segments has a number of contact elements mounted on a surface, each element being spatially separated from adjacent elements. Each of the elements also preferably has spatially separated ridges.

In operation, the device is applied such that the respective surfaces of the contact elements can contact the body of the wearer. In addition, the device flexes in order to contour to the shape of the body and thereby enhancing the surface area that comes into contact with the wearer. Preferably each segment is flexible in order to contour to the shape of the wearer. Likewise, the segments preferably may be linked with flexible linkages such that the linkages flex in accordance with the shape of the body or the movement of the wearer. The device may be worn while the wearer is awake or asleep. As the wearer moves, the device can impart a massaging effect to the covered area. Likewise, the device may apply pressure to the area contacted.

The respective segments preferably may be linked together, either end-to-end, or side-by-side. In the end-to-end linkage embodiment, the segments form a relatively narrow chain which is elongated in a longitudinal direction. This chain is well suited for application adjacent to the spine. In contrast, the side-by-side embodiment is elongated in a horizontal direction. Such an embodiment is well suited for application to a joint, such as an elbow or knee, or for application horizontally across the back, such as to the lower back. Straps can be used in order to affix the device to the body and thereby create a contact pressure or allow the device to be worn when moving about.

The segments also may be linked together using a casing, such as a belt device, into which segments are mounted, using any type of adhesive or strapping means. The casing may then be fastened to a body of a person when the person is in an upright, sitting, lying or walking position. The device also may be used without a casing or other mounting device by simply being placed on a lying body.

In addition, the segments can be used individually, such as for local application on the cervical or lumbar part of the spine.

In a preferred embodiment, at least three contact elements are situated on each of the segments. This number provides mechanical stability such that the segment resists slipping, twisting or other movement.

BRIEF DESCRIPTION OF THE DRAWINGS

The above and other objects and advantages of the invention will be apparent upon consideration of the following detailed description, taken in conjunction with the accompanying drawings in which like reference characters refer to like parts throughout, and in which.

DETAILED DESCRIPTION OF THE INVENTION

Figure 1:
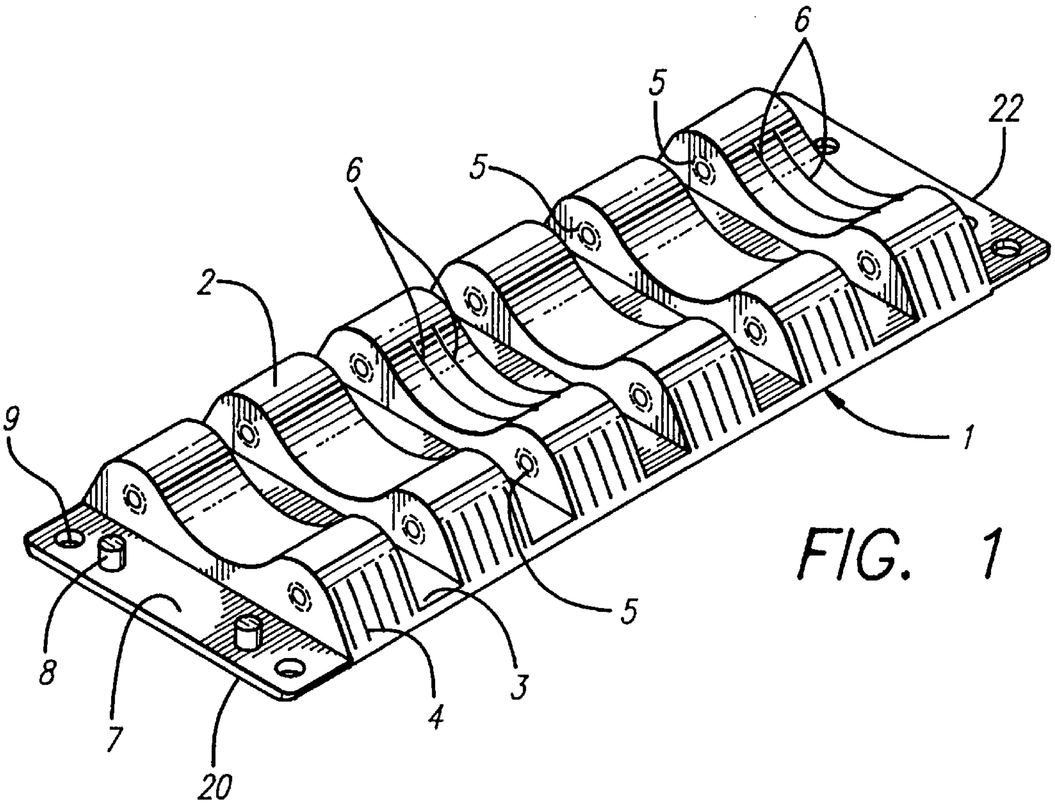
FIG. 1 illustrates a perspective top view of a segment of the device of the present invention.
Figure 3:
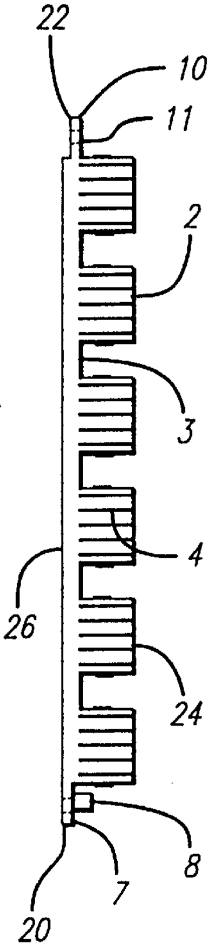
FIG. 3 illustrates a side view of a segment of the device of the present invention.
Figure 6:
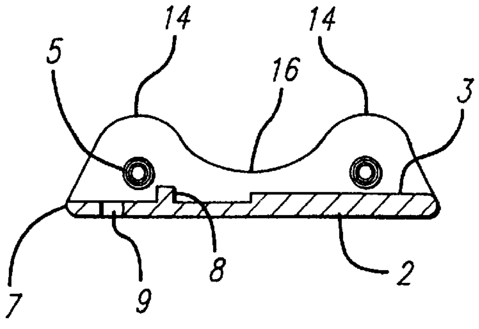
FIG. 6 illustrates a cross-sectional view of a segment of the device in the present invention along section line A—A of FIG. 2.

The treatment device may be constructed of various shapes and sizes. In the preferred embodiment, a plurality of linkable segments are used. The length or width of the device is varied, depending on the arrangement selected for the various linkable segments. As illustrated in FIG. 1, a segment 1 exhibits a plurality of protruding contact elements 2 and recessed surfaces 3 disposed on a first face 24 (i.e. the top face, which contacts the body of the wearer) (FIG. 3) of the segment 1. In the preferred embodiment, the first face 24 of protruding contact elements 2 also may exhibit an undulating shape, where a peak 14 is formed at each lateral end of the protruding element 2, and where a valley 16 is formed between the two peaks 14 (FIG. 6). Any number of peaks 14 may be formed on the first face 24.

The segments 1 may be constructed of any material, such as wood, rubber, plastic or other polymeric materials such as PVC. In the preferred embodiment, the segments 1 are constructed of a material with a relatively low coefficient of heat transfer, such as PVC. By using such a material, the transfer of body heat to the atmosphere is reduced in the localized region to which the segment 1 or linked segments 1 (as described below) are applied. This warming effect itself may be noticeable for some wearers. It is also preferred that the segments 1 be constructed of a material which flexes, so that the segments may contour to the shape of the wearer. This may increase the subjective comfort for the wearer, reduce any risks of abrasion, as well as increase the surface area contacting the wearer.

Any means for linking together the segments may be used. Likewise, any number of segments may be linked together, such as side-by-side or end-to-end, depending upon the area of the wearer's body to which the device is applied. This flexibility enables the device to be used for treatment of the various shaped regions of a body, such as, for example, long narrow areas, such as adjacent the spinal column, or generally tubular areas, such as the neck or limbs.

A preferred linking means provides linking straps which interact with receiving elements on the segments. For example, in the embodiment illustrated in FIGS. 1–4, both holes 9, 11 and pins 8 are provided. The first end 20 of the segment 1 forms a first connection strip 7. The connection strip 7 is provided with two cylindrical pins, 8 and two holes 9. The second end 22 of the segment 1, disposed opposite to the first end 20 forms a second connection strip 10. The second connection strip 10 is provided with two pairs of holes 9 and 11. In this embodiment, the plurality of holes 9, 11 are for receiving straps 32, or alternatively pins 8. Any number of holes or pins may be used to link segments 1. Likewise, the holes 9, 11 may be formed at any position on the segments 1, such as at the side edges or in the middle, as illustrated in FIGS. 12 and 14.

The straps 32 may be constructed of any material, including preferably a stretchable material, although any type of chord also is suitable. The straps may be threaded throughout the holes 9, 11 in order to connect segments 1. Alternatively, when linking two or more segments 1 to each other to form a row 28 of segments, the cylindrical pin 8 of the first connection strip 7 of one segment 1 may be placed into the hole 11 of the second connection strip 10 of a following segment 1.

Figure 9:
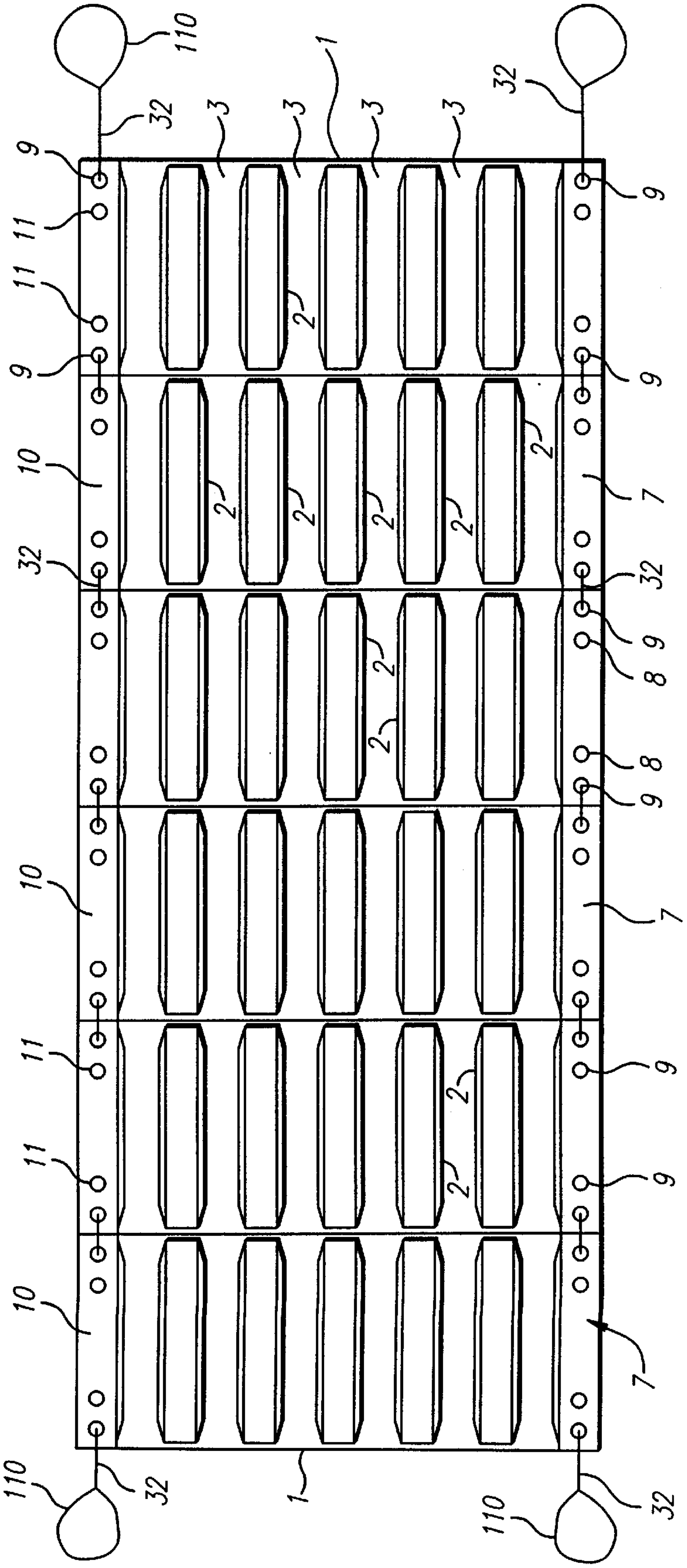
FIG. 9 illustrates an exemplified embodiment of a series of segments of the device of the present invention linked horizontally side-by-side.
Figure 10:
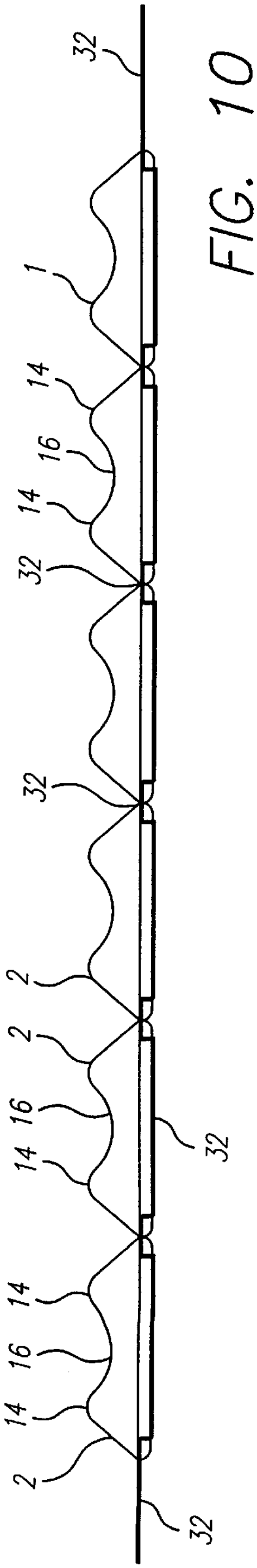
FIG. 10 illustrates an end view of the device illustrated in FIG. 9.
Figure 14:
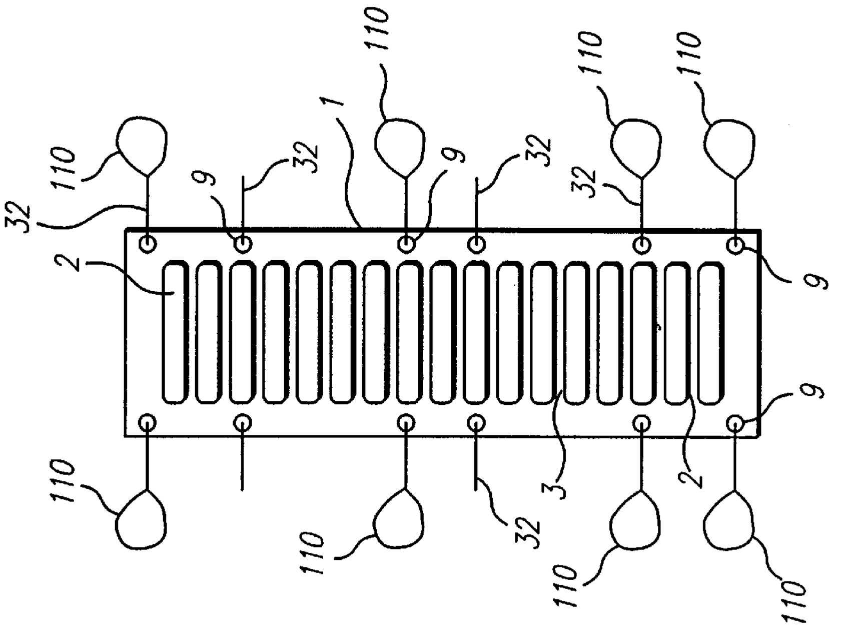
FIG. 14 illustrates an elongated segment of the device of the present invention.
Figure 13:
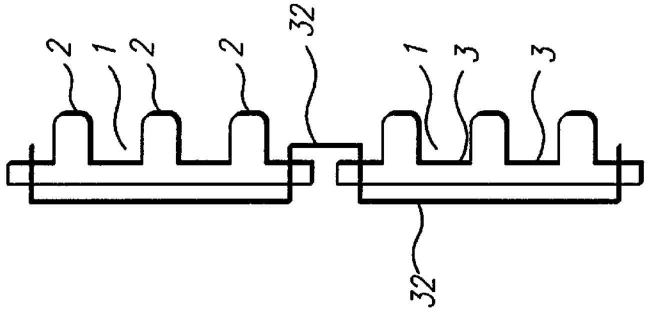
FIG. 13 illustrates a side view of the device illustrated in FIG. 12.
Figure 12:
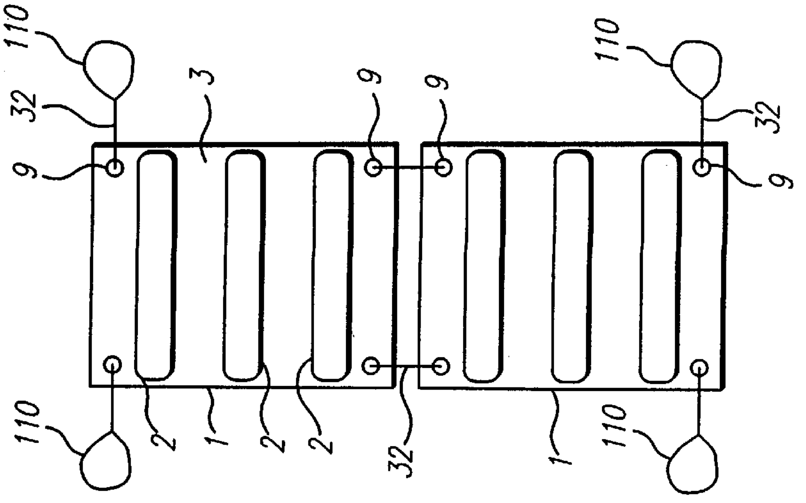
FIG. 12 illustrates an exemplified embodiment of two segments linked end-to-end in accordance with the device of the present invention.

The use of linking straps 32 is also illustrated in FIGS. 9, 10 and 12–14. The linking straps 32 are threaded into and out of holes 9 on segments 1 that are linked together. The segments 1 may be linked together side-by-side by threading a linking strap 32 through holes 9 of horizontally adjacent segments 1, as illustrated in FIGS. 9 and 10. The segments 1 may also be linked together end-to-end by threading a linking strap 32 through holes 9 of vertically adjacent segments, as illustrated in FIGS. 12 and 13. Any other flexible linking means for linking segments may also be used. For example, discrete bands may link adjacent segments by extending through a hole 9 or 11 on one segment 1 and through a hole 9 or 11 on an adjacent segment 1. Likewise, a single segment may be applied using straps, such as illustrated in FIG. 14.

Connecting the segments 1 using flexible linking straps 32 has the advantage that the device may be folded for storage without being disassembled. To store, the device is simply folded, such as like a fan folded map, in the areas where the straps 32 are running between adjacent segments 1.

The device can be worn in contact with the skin of the wearer, or with a separating barrier, such as clothing between the wearer's skin and the device. Likewise, the device may be worn while the wearer is in any position, such as lying down, sitting or moving about. To assist when moving about, the device may be attached to the wearer using straps 32 in conjunction with any fastening means, such as hook-eye fasteners or Velcro® fasteners. For example, if the wearer wishes to use the a plurality of segments linked side-by-side (as illustrated in FIGS. 9 and 10) on the lower back, the straps 32 may extend around the torso and link adjacent the wearer's abdomen.

Figure 7:
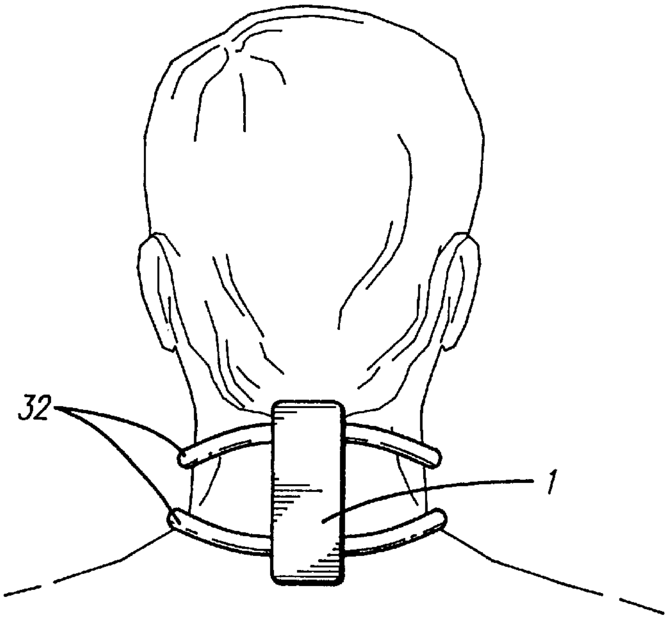
FIG. 7 illustrates an exemplified embodiment of one segment of the device of the present invention placed against the cervical section of the spine.

A single segment 1 may also be fastened to a wearer using straps 32. The single segment may be fastened to any part of the body, such as the neck, as illustrated in FIG. 7.

In a preferred embodiment, illustrated in FIG. 14, an elongated single segment is used. Any number of contact elements 2 may be provided on the single segment 1. In this embodiment, for example, the segment 1 may be elongated so that a greater number of contact elements 2 are provided. The single elongated segment 1 may be used to cover a large region of the wearer, such as the entire spinal region. A theoretical limit on the length of a segment 1 is the length of the longest contiguous portion of a user's body, typically the spine. However, even where there is excess length, the excess may simply dangle, such as below the spine.

In a preferred embodiment, illustrated in FIGS. 12 and 13, each segment 1 has at least three contact elements 2. This number provides mechanical stability such that the segment 1 can resist slipping, twisting or other movement. While increasing the number of contact elements 2 may enhance stability, a reduced number of contact elements 2, and therefore size of the segments 1, increases the multitude of different combinations of segments possible. For example narrower areas of a wearer can be covered using smaller segments 1 than in using larger segments.

A row 28 of segments 1 can be used for treatment of the whole spine. A desired number of segments 1, forming the row 28, are placed along the spine of a person in a horizontal position, wherein the peaks 14 of the protrusions 2 of the segments 1 are placed on either side of the spine, thereby contouring the shape of the vertebral column. This end-to-end arrangement of the segments 1 may be accomplished by any means, including using the pins 8, holes 9, 11 and straps.

Figure 8:
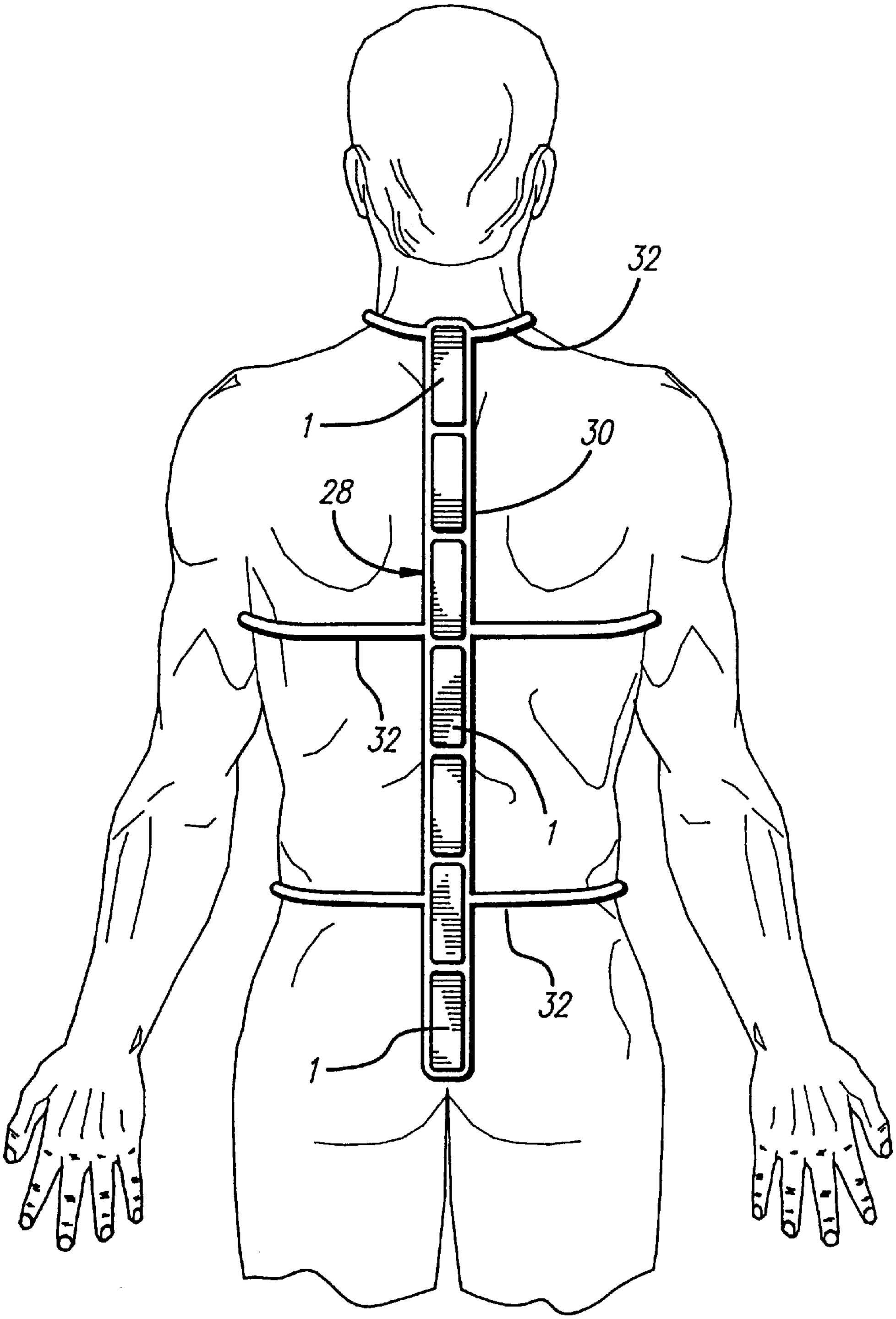
FIG. 8 illustrates an exemplified embodiment of a series of segments of the device of the present invention linked longitudinally end-to-end and disposed in a casing and applied against the length of the spine.

As illustrated in FIG. 8, the row 28 of segments 1 can be placed into a casing 30. The casing 30 includes fastening straps 32 placed at a distance from each other on the two lateral sides of the casing 30. The casing 30, including the row 28 of segments 1, can be placed against the spinal column of a wearer and fastened to the body of wearer by the fastening straps 32, thereby allowing the wearer to wear the device while in an upright position, i.e. the device can be worn while the wearer can pursue any desired activity.

If it is not necessary to treat the entire length of the spine, it is possible to place the desired number of segments 1 into a casing 30, having a length corresponding to the number of segments 1, and to fasten the casing 30 including the desired number of segments 1, covering the desired part of the spine to be treated, with the fastening straps 32 to the body of the person. An illustration of the employment of one segment 1 in a casing 30 is shown in FIG. 7.

Any type of casing 30 may be used. Preferably, the casing backing 90 is made of a flexible material so as to contour to the shape of the wearer. Fastening the segments 1 into the casing may also be accomplished by any means. For example, the segments may be attached to the casing 1 using Velcro® or other removable-adhesive material 100, or permanently, such as by using thread or an adhesive. In the embodiment in which the segments 1 are attached using Velcro®, a portion of the Velcro® 100 is fastened to the casing backing 90 and another portion is attached to the second faces 26 of the segments 1, thereby enabling the segments 1 to be fastened to the casing backing 90.

The desired number of segments 1 are attached to the casing 30 and the casing is attached to the user using straps 32. Likewise, the free ends of the straps 32 may fasten using any fastening means 110, such as hook-eye fasteners or Velcro®. Alternatively, the casing itself may have flaps 120, 125 that have no fastened segments. The flaps 120, 125 may fasten to one another using any fastening means. For example, when the casing is used to place the device on a tubular portion of a body, the flaps extend around the body portion and fasten on the side generally opposite the segments 1. Likewise, the casing 30 itself may be made of a stretch material and be tubular. Thus a wearer could simply slide the tubular casing 30 over a desired body part, as illustrated in FIG. 11A, which shows the casing 30 over a knee.

Figure 11:
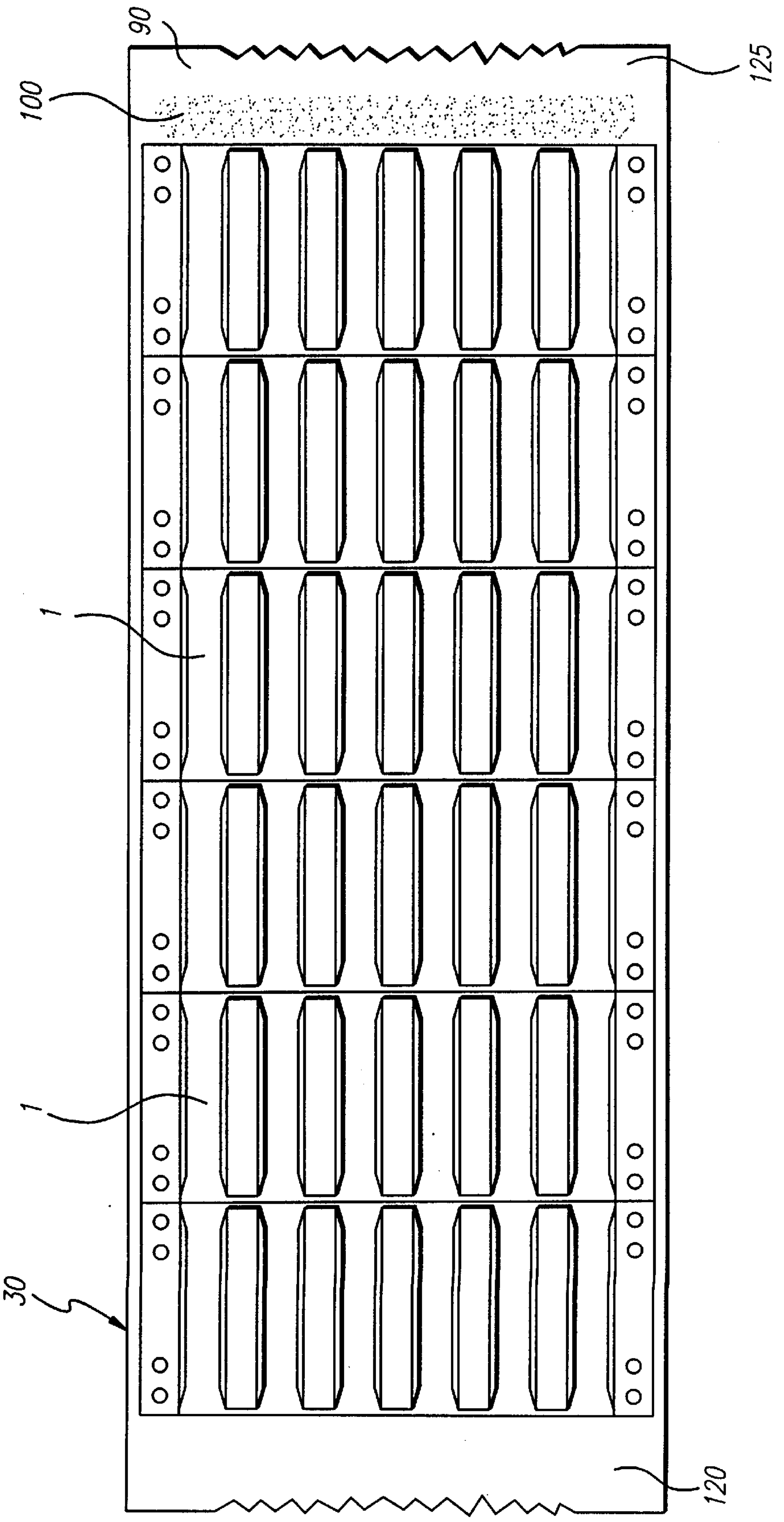
FIG. 11 illustrates an exemplified embodiment of a series of segments of the device of the present invention linked horizontally side-by-side and disposed in a casing.
Figure 11A:
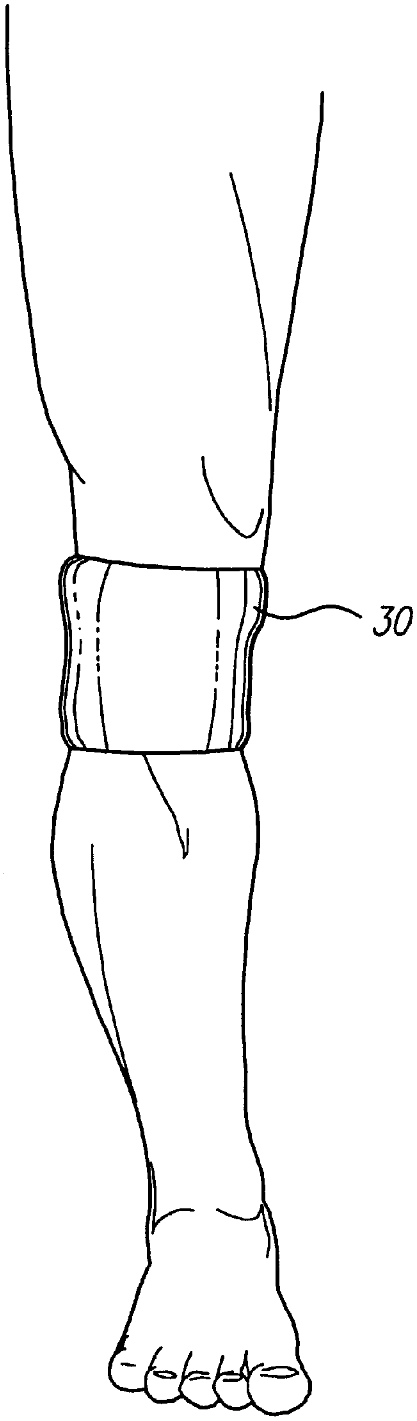
FIG. 11A illustrates a tubular casing embodiment of the device of the present invention.

In an alternative embodiment, as illustrated in FIG. 11, any number of segments 1 may be placed side-by-side in a casing 30. The segments may be attached to the casing using the removable-adhesive material 100, straps, or alternatively, permanently, such as by sewing.

Figure 2:
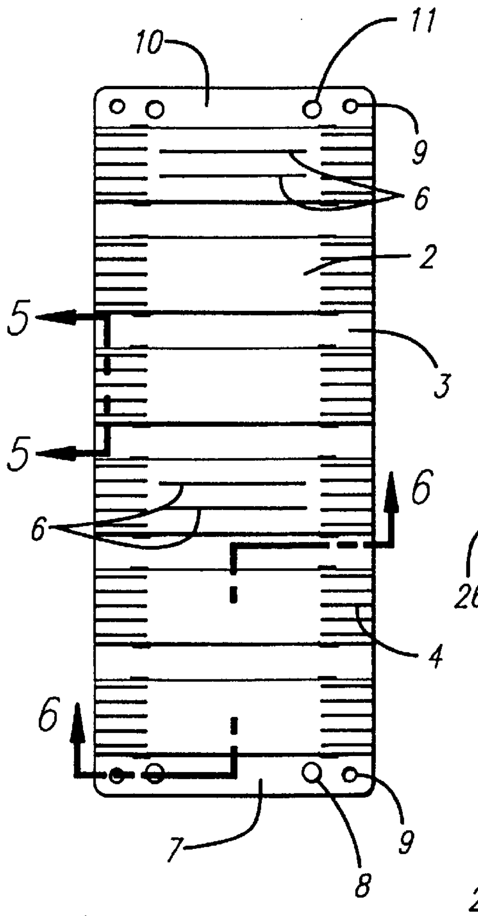
FIG. 2 illustrates a planar view of a segment of the device of the present invention.
Figure 4:
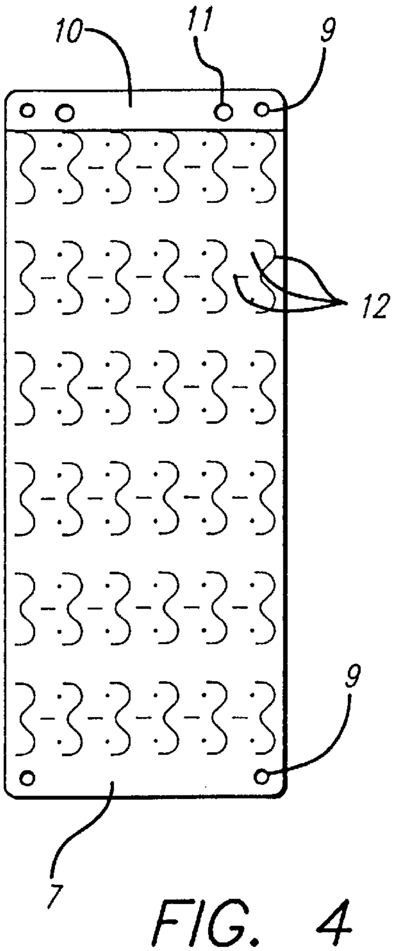
FIG. 4 illustrates a bottom view of a segment of the device of the present invention.
Figure 5:
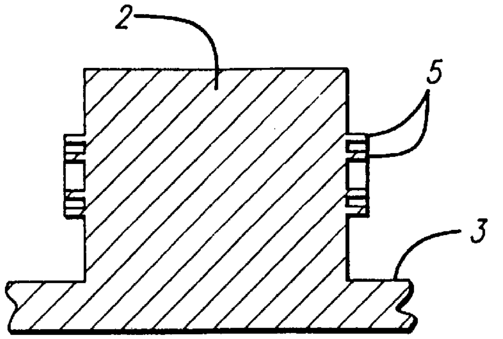
FIG. 5 illustrates a cross-sectional view of a segment of the device of the present invention along section line B—B of FIG. 2.

In a preferred embodiment the two ends of each protruding element 2 exhibit on their outer end surfaces a plurality of carved notches and grooves (engravings) 4. These notches and grooves 4 may contribute to ease of storage of the segments by creating a smaller side surface area for adhesion. Likewise, in use, they may promote a more efficient heat transfer along the side edges of the segments by promoting a piping effect, such as when pressure causes the contact elements 2 to press into the surface of the wearer's body. Also, as illustrated in FIG. 2, two grooves 6 may be disposed in the valley 16 of each third protruding element 2. These grooves may also promote heat transfer as well as reduce sticking to the wearer, when the device is worn in contact with the skin. A cylindrical outlet projection 5, illustrated in FIG. 5, may be disposed concentrically in the curve of each peak 14 on the longitudinal faces of the protruding element 2. These outlet projections also may help to avoid sticking to the wearer. As illustrated in FIG. 4, the segment 1 exhibits a plurality of projections, notches, and outlets 12, shaped as lines and dots, on the second face 26. These elements may assist with storage of the device by reducing the possibility of segments 1 sticking to each other.

Thus, it is seen that a linkably segmented device having protruding contact elements is provided. One skilled in the art will appreciate that the present invention can be practiced by other than the preferred embodiments which are presented for purposes of illustration and not by way of limitation, and the present invention is limited only by the claims which follow.

What is claimed is:

1. A device for being positioned on the body of a person comprising:

- a plurality of linkable segments including a first segment, wherein each of the segments comprises:
  - a discrete mounting structure elongated in a longitudinal direction and defining at least one aperture;
  - a plurality of contact elements protruding from and fixedly attached to the mounting structure, wherein the contact elements are longitudinally spaced apart from each other on the mounting structure, each of the elements including:
    - a top face generally opposite the mounting structure: and
    - a plurality of peaks on the top face, each peak having a summit and downwardly directed sides; and the device further comprising:
      - a linking strap for linking the segments together in a row wherein the linking strap is threaded through at least one aperture defined in the surface of the first segment and through at least one aperture defined in the surface of an adjacent segment.

2. The device of claim 1 wherein the respective mounting structure of each segment includes:

- a first longitudinal edge; and
- a second longitudinal edge at its opposite end;
- wherein, the contact elements are longitudinally spaced from one another and at least one said aperture defined in the respective mounting structure of each segment adjacent each of the first and second longitudinal edges; and
- wherein, the linking strap is threaded through at least one aperture adjacent the first longitudinal edge of the first segment and through an aperture adjacent the first longitudinal edge of the adjacent segment.

3. The device of claim 1 wherein the mounting surface is elongated in a lateral direction generally perpendicular to the longitudinal direction and the linking strap links adjacent segments laterally side-by-side.

4. The device of claim 3 further comprising a first linking strap and a second linking strap, wherein the respective mounting structure of each segment includes:

- a first longitudinal edge; and
- a second longitudinal edge at its opposite end;
- wherein, the contact elements are longitudinally spaced from one another and at least one said aperture defined in the respective mounting structure of each segment adjacent each of the first and second longitudinal edges; and wherein,
- the first linking strap is threaded through at least one aperture adjacent the first longitudinal edge of the first segment and through an aperture adjacent the first longitudinal edge of the adjacent segment; and the second linking strap is threaded through at least one aperture adjacent the second longitudinal edge of the first segment and through an aperture adjacent the second longitudinal edge of the adjacent segment.

5. The device of claim 4 further comprising a second segment, wherein:

The first segment is at one end of the row and the second segment is at the opposite end of the row;

each of the first and second segments has a free end opposite the end adjacent to its respective adjacent linked segment;

each of the first and second linking straps has opposite free ends extending respectively from the free ends of the first and second segments;

the respective free ends of the first and second linking straps are linkable in any combination with each other for retaining the device on the wearer.

6. The device of claim 1 wherein each segment is longitudinally elongated and wherein the linking strap links the segments longitudinally end-to-end and the linking strap connects adjacent segments.

7. The device of claim 1 wherein said linking strap is flexible, making the linked segments foldable at the linking straps.

8. The device of claim 1 wherein the linking strap comprises a stretchable chord.

9. The device of claim 1 wherein at least one of the linkable segments is made of a polymeric material.

10. The device of claim 1 wherein each of the linkable segments is made of PVC.

11. The device of claim 1 wherein each segment further comprises at least three contact elements.

12. The device of claim 1 wherein:

the peaks on each of the respective elements are arranged in at least one row;

the peaks in each said row are spatially separated from one another by a fixed distance; and the peaks in each of said rows are longitudinally aligned wherein at least two columns are formed by the peaks in adjacent elements.

13. The device of claim 1 wherein each of said segments includes lateral sides, said linking strap linking the segments together side-by-side in a lateral row.

14. The device of claim 1 wherein each of said segments includes longitudinal ends, said linking strap linking the segments together end-to-end in a longitudinal row.

15. A therapeutic device for being positioned on a user's body comprising:

at least one segment wherein each segment comprises:

a discrete mounting structure elongated in a longitudinal direction and including a mounting surface;

a plurality of elements fixedly attached to and protruding from the mounting structure, wherein:

each of the elements has a top face opposite the mounting surface and said top face has an undulating shape with a plurality of peaks;

each peak has a summit and downwardly sloping sides; and a strap means for retaining the device on the user's body including means engaging the mounting structure and at least two free strap ends, the free ends being fastenable to one another.

16. The device of claim 15 wherein the mounting structure includes at least one strap receiving element wherein the at least one strap receiving element comprises a plurality of apertures defined in the mounting structure wherein the strap means comprises at least one flexible chord for being threaded through at least one said strap receiving element.

17. The device of claim 15 wherein the mounting structure includes at least one strap receiving element wherein the at least one strap receiving element comprises a first adhering material and wherein the strap means comprises a second adhereing material that adheres to the first adhereing material.

18. The device of claim 17 wherein the mounting structure further comprises: a front side to which the contact elements are fixedly attached; and a rear side to which the first removably adhering material is fixedly attached.

19. The device of claim 17 wherein the first adhereing material and the second adhereing material is selected from a group consisting of chemical adhesive and hook and loop fasteners.

20. The device of claim 15 wherein:

the peaks on each of the respective elements are arranged in at least one row;

the peaks in each said row are spatially separated from one another by a fixed distance; and the peaks in each of said rows are longitudinally aligned wherein at least two columns are formed by the peaks in adjacent elements.

21. The device of claim 15 wherein each of the plurality of elements is integrally formed with the mounting structure forming a unitary one-piece structure including the elements and the mounting structure.

22. A therapeutic device for being positioned on a user's body comprising:

at least one segment wherein each segment comprises:

a discrete mounting structure elongated in a longitudinal direction and including a mounting surface;

a plurality of elements fixedly attached to and protruding from the mounting structure, wherein:

each of the elements has a top face opposite the mounting surface and said top face has an undulating shape with a plurality of peaks;

each peak has a summit and downwardly sloping sides; and the elements are longitudinally spaced apart from one another on the mounting surface; and a casing operatively connected to the segments.

23. The device of claim 22 wherein the casing includes a casing backing, having an inner and outer mounting structure, and the segments are fastened on the inner mounting structure.

24. The device of claim 22 wherein:

the peaks on each of the respective elements are arranged in at least one row;

the peaks in each said row are spatially separated from one another by a fixed distance; and the peaks in each of said rows are longitudinally aligned wherein at least two columns are formed by the peaks in adjacent elements.

25. The device of claim 22 wherein each of the plurality of elements is integrally formed with the mounting structure forming a unitary one-piece structure including the elements and the mounting structure.

26. The device of claim 22 wherein said casing further comprises a fastening means for mounting said segments to the casing.

27. The device of claim 26 wherein the fastening means comprises a removable adhesive material.

28. The device of claim 17 wherein:

mounting structure comprises a first side and second side wherein the contact elements protrude from the first side;

a first portion of the removable adhesive material is mounted to the casing backing and a second portion of the removable adhesive material is mounted on the second side of the mounting structure of each respective segment.

29. The device of claim 22 wherein the casing comprises:

an inner casing surface; and a fastening means mounting the segments to the inner casing surface.

30. The device of claim 22 wherein the casing further comprises:

a casing backing;

a fastening means for mounting segments to the casing backing, wherein the segments are mounted side-by-side to the casing backing.

31. The device of claim 30 wherein the casing backing is made of a flexible material.

32. The device of claim 22 wherein the device comprises a plurality of said segments each having lateral sides, said segments being positioned laterally side-by-side on said casing.

33. The device of claim 22 comprising a plurality of said segments each having longitudinal ends, said segments being positioned longitudinally end-to-end on said casing.

34. A therapeutic device for being positioned on a user's body comprising:

at least one segment wherein each segment comprises:

a discrete mounting structure elongated in a longitudinal direction and including a mounting surface;

at least one aperture defined in said mounting structure;

a plurality of elements fixedly attached to and protruding from the mounting structure, wherein:

each of the elements has a top face opposite the mounting surface and said top face has an undulating shape with a plurality of peaks;

each peak has a summit and downwardly sloping sides; and a first fastening strap threaded through a first of said at least one aperture.

35. The device of claim 34 including:

at least two of said apertures; and a second fastening strap threaded through a second of said apertures, said second fastening strap cooperating with said first fastening strap to retain the device on the body.

* * * * *